(12) United States Patent
Shah

(10) Patent No.: US 9,655,369 B2
(45) Date of Patent: May 23, 2017

(54) PESTICIDAL COMPOSITION COMPRISING SULPHUR, ACARICIDE AND AN AGROCHEMICAL EXCIPIENT

(76) Inventor: Deepak Pranjivandas Shah, Mumbai (IN)

( * ) Notice: Subject to any disclaimer, the term of this patent is extended or adjusted under 35 U.S.C. 154(b) by 509 days.

(21) Appl. No.: 13/981,619

(22) PCT Filed: Jan. 30, 2012

(86) PCT No.: PCT/IN2012/000068
§ 371 (c)(1),
(2), (4) Date: Sep. 11, 2013

(87) PCT Pub. No.: WO2012/101661
PCT Pub. Date: Aug. 2, 2012

(65) Prior Publication Data
US 2014/0004167 A1    Jan. 2, 2014

(30) Foreign Application Priority Data
Jan. 28, 2011  (IN) .......................... 253/MUM/2011

(51) Int. Cl.

| | |
|---|---|
| *A01N 59/02* | (2006.01) |
| *A01N 53/00* | (2006.01) |
| *A01N 47/24* | (2006.01) |
| *A01N 43/12* | (2006.01) |
| *A01N 43/54* | (2006.01) |
| *A01N 43/56* | (2006.01) |
| *A01N 43/78* | (2006.01) |
| *A01N 43/90* | (2006.01) |

(52) U.S. Cl.
CPC ............ *A01N 59/02* (2013.01); *A01N 43/12* (2013.01); *A01N 43/54* (2013.01); *A01N 43/56* (2013.01); *A01N 43/78* (2013.01); *A01N 43/90* (2013.01); *A01N 47/24* (2013.01); *A01N 53/00* (2013.01)

(58) Field of Classification Search
None
See application file for complete search history.

(56) References Cited

U.S. PATENT DOCUMENTS

| 6,090,415 A | 7/2000 | Stadler et al. |
| 7,194,964 B2 * | 3/2007 | Tidow .................... A01N 59/02 111/118 |
| 7,635,404 B1 | 12/2009 | Devic et al. |

FOREIGN PATENT DOCUMENTS

| CN | 101310582 A | 11/2008 |
| CN | 101857482 A | 10/2010 |
| WO | 2004/026033 A1 | 4/2004 |

OTHER PUBLICATIONS

Bretscneider et al. (Chimia, 57, 697-701, 2003) Spirodiclofen and Spiromesifen—Novel Acaricidal . . . .*
Reddy, S.G.E., & Kumar, N.K.K., "Integrated Management of Two-Spotted Spider Mite, Tetranychus Urticae (Koch) on Tomato Grown Under Polyhouse", Pest. Res. J., 2006, 18, 162-165 , Abatract , col. 1-4.
Tomlin, C.D.S (Ed.)., The Pesticide Mannual, 15th ed., 2009, BCPC: Hampshire, UK Entries 1, 81, 83, 353, 368, 467, 785, 786, 801.
Sarmah, M, et al.; Bioefficacy of Insecticides in Combination with Acaricides and Nutrients Against He/ope/tis Theivora Waterhouse in Tea; Pesticide Research Journal vol. 18(2): 141-145. Dec. 2006.
Achrya, S., et al.; Efficacy of insecticides against Okra Jassid, Amrasca biguttula biguttula Ishida [Sep. 2002]; http://agris.fao.org/agris-search/search.do?recordID=IN2005001133.

* cited by examiner

*Primary Examiner* — Tigabu Kassa
(74) *Attorney, Agent, or Firm* — Veritay Group, IP; Susan B. Fentress

(57) ABSTRACT

The present invention relates to a pesticidal composition comprising an effective amount of sulphur, an effective amount of at least one acaricide selected from the group consisting of bifenazate, fenpyroximate, fenazaquin, hexythiazox, spirodiclofen, spiromesifen and their salts thereof and at least one agrochemically acceptable excipient.

7 Claims, No Drawings

PESTICIDAL COMPOSITION COMPRISING SULPHUR, ACARICIDE AND AN AGROCHEMICAL EXCIPIENT

BACKGROUND OF THE INVENTION

1. Field of the Invention

The present invention relates to a pesticidal composition comprising an effective amount of sulphur, an effective amount of at least one acaricide or its salts, and at least one agrochemically acceptable excipient. The invention further relates to a method of application of the pesticidal composition to the crops.

2. Description of the Related Art

The role of elemental sulphur as a pesticide has been known for a long time. The role of sulphur in controlling, inhibiting and eradicating the growth of fungi such as mildews and mites are well known. Sulphur is mostly available in its elemental form and different formulations such as granules, pellets, powders, etc. are known for providing sulphur in a form for use as a fertilizer or pesticide. Sulphur formulations used alone are good to moderately effective against powdery mildew and mites. They are also used as clean up applications for hibernating mites populations before the onset of plant protection schedules in horticultural and perennial crops like tea. Sulphur not only works as an acaricide, for example on mites but is also used as a supplementary plant nutrient.

Further demands on insecticidal and acaricidal compounds include reduced phytotoxicity, reduced dosage, substantial broadening of spectrum and increased safety, to name a few.

The biological properties of known compounds are not entirely satisfactory in the areas of pest control, phytotoxicity, and environmental and worker exposure, for example. In particular, it has been observed that the pests become resistant to the pesticides which are at times administered in higher dosages to achieve the desired control, thereby leading to soil toxicity and other environmental hazards besides higher costs.

Hence, there is a need to develop a composition which addresses the problem of resistance and soil toxicity and also is used at reduced dosages, controls environmental damage, offers broader crop protection spectrum, improved and healthy foliage, rainfastedness, improved crop yield, saves labour and control against various insects and pests, improves plant growth and is yet cost-effective to the end user.

SUMMARY OF THE INVENTION

It has now been discovered that a pesticidal composition comprising an effective amount of sulphur, an effective amount of at least one acaricide selected from the group consisting of, bifenazate, fenpyroximate, fenazaquin, hexythiazox, spirodiclofen, spiromesifen or their salts, and at least one agrochemically acceptable excipient has unexpectedly high activities in the control of various pests and insects for example, Lepidoptera, termites etc.

It has also been determined that a pesticidal composition comprising sulphur in the range from 30% to 80%, bifenthrin or its salts in the range from 1.5% to 10% of the total weight of the composition, and at least one agrochemically excipient additive demonstrates excellent control over certain pests, for e.g. sucking pests, chewing pests and mite populations.

Surprisingly, the inventors of the application have discovered that a pesticidal composition comprising sulphur in the range from 32.5% to 90%, abamectin is in the range from 0.08% to 3.6% and its salts thereof and at least one agrochemically acceptable excipient demonstrates surprisingly excellent efficacy and synergistic effect with prolonged management of mites.

The pesticidal compositions offers a broad spectrum of protection, addresses the concerns of resistance, improves foliage, improves rainfastedness and in various instances, improves crop yield and grain quality. The compositions disclosed herein, also serve as an intervention application between very specific actives, which alone are likely to lead to resistance in areas of epidemic and high frequency of pesticidal application.

Quite advantageously, in certain cases, it has been observed, that the compositions at very low concentrations of the active ingredients can be effectively applied, thereby reducing the burden on the environment. In certain cases, it has also been noted that the compositions at lower rates of the active ingredients in combination together provided a longer duration of control of the pest.

DETAILED DESCRIPTION

In describing the embodiments of the invention, specific terminology is resorted for the sake of clarity. However, it is not intended that the invention be limited to the specific terms so selected and it is to be understood that each specific term includes all technical equivalents that operate in a similar manner to accomplish a similar purpose.

The present invention relates to a pesticidal composition comprising an effective amount of sulphur, an effective amount of at least one acaricide selected from the group consisting of, bifenazate, fenpyroximate, fenazaquin, hexythiazox, spirodiclofen, spiromesifen or their salts, and at least one agrochemically acceptable excipient.

According to an embodiment, sulphur is present in the composition in a range from 25% to 90% of the total composition. According to an embodiment, the acaricide is present in the composition in a range from 0.75% to 30% of the total composition.

The pesticidal composition can be in a solid form or a liquid form. For example, the pesticidal composition may be in the form emulsion concentrates, wettable powders, suspension concentrates, suspoemulsions, microemulsions, capsulated suspension, water dispersible granules, pellets, seed dressings, emulsions for seed treatment, of gels, emusions in water, oil dispersions, etc Preferably, the pesticidal composition is in the form of water dispersible granules. When the composition is in the form of water dispersible granules, usually sulphur is present in the range from 50% to 80% and the acaricide is present in the range from 1% to 30% of the total composition.

Preferably, the pesticidal composition is in the form of suspension concentrates. When the composition is in the form of suspsension concentrate, usually sulphur is present in the range from 25% to 80% and the acaricide is present in the range from 0.75 to 10% of the total composition.

Water dispersible granules can be defined as a pesticide formulation consisting of granules to be applied after disintegration and dispersion in water. As described herein, "WG" or "WDG" refer to water dispersible granules.

Suspension concentrate can be defined as a stable suspension of solid pesticides in a fluid usually intended for dilution with water before use. As described herein, "SC" refers to suspension concentrates.

As defined herein, WP refers to a wettable powder, which can be a powder formulation to be applied as a suspension after dispersion in water. As defined herein, EC refers to an emulsifiable concentrate, which can be a liquid homogenous formulation to be applied as an emulsion after dilution in water.

As described herein, "DAS" refer to Days After Spray.

According to an embodiment, sulphur is in the range from 30% to 80% and bifenazate is in the range from 5% to 15% of the total weight of the composition. According to another embodiment, sulphur is in the range from 60% to 80% and bifenazate is in the range from 6% to 15% of the total weight of the composition in the form of water dispersible granules. According to another embodiment, sulphur is in the range from 30% to 80% and bifenazate is in the range from 5% to 7.5% of the total weight of the composition in the form of suspension concentrate.

According to an embodiment, sulphur is in the range from 32.5% to 90% and fenpyroximate is in the range from 0.75% to 4% of the total weight of the composition. According to another embodiment, sulphur is in the range from 65% to 90% and fenpyroximate is in the range from 1% to 4% of the total weight of the composition in the form of water dispersible granules. According to another embodiment, sulphur is in the range from 32.5% to 75% and fenpyroximate is in the range from 0.75% to 6% of the total weight of the composition in the form of suspension concentrate.

According to an embodiment, sulphur is in the range from 30% to 80% and fenazaquin is in the range from 5% to 30% of the total weight of the composition. According to another embodiment, sulphur is in the range from 55% to 80% and fenazaquin is in the range from 10% to 30% of the total weight of the composition in the form of water dispersible granules. According to another embodiment, sulphur is in the range from 30% to 70% and fenazaquin is in the range from 5% to 9.5% of the total weight of the composition in the form of suspension concentrate.

According to an embodiment, sulphur is in the range from 30% to 90% and hexythiazox is in the range from 0.75% to 4% of the total weight of the composition. According to another embodiment, sulphur is in the range from 60% to 90% and hexythiaxoz is in the range from 1% to 4% of the total weight of the composition in the form of water dispersible granules. According to another embodiment, sulphur is in the range from 30% to 70% and hexythiaxoz is in the range from 0.75% to 4% of the total weight of the composition in the form of suspension concentrate.

According to an embodiment, sulphur is in the range from 30% to 85% and spirodiclofen is in the range from 2.5% to 15% of the total weight of the composition. According to another embodiment, sulphur is in the range from 60% to 80% and spirodiclofen is in the range from 5% to 15% of the total weight of the composition in the form of water dispersible granules. According to another embodiment, sulphur is in the range from 30% to 70% and spirodiclofen is in the range from 2.5% to 10% of the total weight of the composition in the form of suspension concentrate.

According to an embodiment, sulphur is in the range from 25% to 80% and spiromesifen is in the range from 2.5% to 12% of the total weight of the composition. According to another embodiment, sulphur is in the range from 50% to 80% and spiromesifen is in the range from 4% to 12% of the total weight of the composition in the form of water dispersible granules. According to another embodiment, sulphur is in the range from 25% to 75% and spiromesifen is in the range from 2.5% to 10% of the total weight of the composition in the form of suspension concentrate.

The invention further relates to a pesticidal composition comprising sulphur in the range from 30% to 80%, bifenthrin in the range from 1.5% to 7% of the total weight of the composition and at least one agrochemically acceptable excepient. According to another embodiment, sulphur is in the range from 60% to 80% and bifenthrin is in the range from 3% to 7% of the total weight of the composition in the form of water dispersible granules. According to another embodiment, sulphur is in the range from 30% to 70% and bifenthrin is in the range from 1.5% to 7% of the total weight of the composition in the form of suspension concentrate.

The invention further relates to a pesticidal composition comprising sulphur in the range from 32.5% to 90%, abamectin in the range from 0.08% to 3.6% of the total weight of the composition and at least one agrochemically acceptable excipient. According to an embodiment, sulphur is in the range from 65% to 90% and abamectin is in the range from 0.08% to 3.6% of the total weight of the composition in the form of water dispersible granules. According to another embodiment, sulphur is in the range from 32.5% to 80% and abamectin is in the range from 0.75% to 3% of the total weight of the composition in the form of suspension concentrate.

According to yet another embodiment, the at least one agrochemically acceptable additive can comprise surfactants including wetting agents and/or dispersing agents, emulsifiers, fillers, diluents, solvents, coating agents and stabilizers. However, those skilled in the art will appreciate that it is possible to utilize additional agrochemically acceptable additives without departing from the scope of the present invention. The agrochemically acceptable additives are in the range from 7% to 70% of the total weight of the composition.

Wetting agents which can be commonly used include sulfosuccinates, naphthalene sulfonates, sulfated esters, phosphate esters, sulfated alcohol and alkyl benzene sulfonates. However, those skilled in the art will appreciate that it is possible to utilize other wetting agents known in the art without departing from the scope of the invention.

Dispersing agents which can be commonly used include polycarboxylates, naphthalene sulfonate condensates, phenol sulfonic acid condensates, lignosulfonates, methyl oleyl taurates and polyvinyl alcohols. However, those skilled in the art will appreciate that it is possible to utilize other dispersing agents known in the art without departing from the scope of the invention.

Emulsifiers can be of the anionic, cationic or non-ionic type. Emulsifiers which do not cause the liquid active substance to solidify are particularly preferred. Some liquid actives are completely miscible in water and may not require an emulsifier. These emulsifiers are usually used in admixture. The emulsifiers which are commonly used include ethoxylated and ethopropoxylated alcohols and nonyl phenols, ethoxylated tristeryl phenol, ethoxylated tristeryl phenol phosphates, ethoxylated and ethopropoxylated castor oil, calcium alkyl benzene sulfonates and proprietary blended emulsifiers. However, those skilled in the art will appreciate that it is possible to utilize other emulsifiers known in the art without departing from the scope of the invention.

Fillers which can be commonly used include diatomaceous earth, kaolin, bentonite, precipitated silica, attapulgite, and perlite. However, those skilled in the art will appreciate that it is possible to utilize other fillers known in the art without departing from the scope of the invention Diluents which can be commonly used include one or more of tone calcite, mica, soap powder, dolomite and lactose. However, those skilled in the art will appreciate that it is possible to utilize other diluents known in the art without departing from the scope of the invention.

Solvents which can be commonly used include one or more of N,N-dimethyl decanamide, N-methylpyrrolidone, cyclohexanone, dimethyl formamide, tetrahydrofuran, dimethylsulfoxide, petroleum distillates and chlorobenzenes. However, those skilled in the art will appreciate that it is possible to utilize other solvents known in the art without departing from the scope of the invention.

The compositions comprising sulphur and an acaricide can be prepared by various processes. Water dispersible granule compositions can be made by various processes such as spray drying, fluid bed spray granulation, extrusion, pan granulation, etc. One way of making water dispersible granular compositions which include sulphur and the acaricide involves initially blending required additives such as wetting agents, dispersing agents, emulsifiers, solvents, fillers to obtain an additive mix. The additive mix obtained is dispersed in sufficient quantity of water to form a blend. A requisite amounts of acaricide technical and sulphur technical are slowly added to the blend by high shear mixing. Further agrochemically acceptable excipients such as fillers can be added, if required to form a mixture. The above mixture is wet milled using various mill for example a bead mill to obtain an average particle size of less than 50 microns, preferably less than 15 microns, preferably 1 to 10 microns to obtain the mill base.

The mill base is granulated in an appropriate drying system for example spray drier or other drying methods with an outlet of a suitable with an out let of a suitable temperature followed by sieving to remove the under sized and oversized granules, to obtain WG formulation comprising sulphur and acaricide in combination. There are various other methods to make WG formulation such as fluid bed spray granulation, extrusion, pan granulation etc Alternately stable aqueous suspension concentrates compositions of sulphur and the acaricide may be prepared by blending required additives such as wetting agents, dispersing agents, emulsifiers, fillers to obtain an additive mix. Then a mill base having an average particle size of less than 50 microns, preferably less than 15 microns, preferably 1 to 10 microns is prepared by milling a mixture of requisite amount of the acaricide and sulphur technical in appropriate ratios of additive mix in required amount of water containing solvent. Further, sufficient quantity of water with required amounts of binders and preservatives is added to the mill base and mixed thoroughly to get SC formulations of the desired combination of sulphur and the acaricide.

Alternately, wettable powder compositions of sulphur and solid acaricide can be prepared by blending required additives such as wetting agents, dispersing agents, emulsifiers, fillers to obtain an additive mix. Further essential amount of sulphur and acaricide technical are blended thoroughly with 10 parts by weight of additive mix, 5 parts of a carrier and the required amount of filler. The mixture is then micronised using a suitable mill like fluid energy mill; to an average particle size of less than 50 microns, preferably less than 15 microns, preferably 4 to 10 microns to get the WP formulation comprising sulphur and acaricide in combination.

The wettable powder compositions of sulphur and liquid acaricide can be prepared by blending required additives such as wetting agents, dispersing agents, emulsifiers, fillers to obtain an additive mix. An essential quantity of sulphur technical, additive mix and optionally filler are blended together and are then micronised using a suitable mill like fluid energy mill to an average particle size of less than 50 microns, preferably less than 15 microns, preferably 4 to 10 microns to obtain sulphur base. The requisite amount of liquid pesticide is then absorbed on carrier to obtain acaricide base. The proportionate amount of the acaricide base and the sulphur base are blended thoroughly to get WP formulation.

Alternately, emulsifiable concentrate compositions can be prepared by dissolving required quantity of the acaricide in a solvent to obtain a solution. A blend of non ionic and an anionic emulsifier are added to the solution to obtain the EC of the acaricide.

According to an embodiment, the invention relates to a method of application of an effective amount of the pesticidal composition, wherein the composition is applied to crops through foliar spray.

Through the agrochemical composition the number of applications to control wide range of pests appearing at the same time is minimized. The composition is highly safe to the user and to the environment. The composition also is cost-effective, as it provides much greater simultaneous control and can be used in a variety of crops with a broader spectrum of protection improved and healthy foliage, rainfastness, improved crop yield, better grain quality. The composition is thereby rendered highly economical and beneficial to the end-users when compared to the standalone compositions of the acaricide and sulphur. Also, the compositions serve as an intervention application between very specific actives which alone are likely to lead to resistance in areas of epidemic and high frequency of pesticidal applications.

EXAMPLES

Examples for Sulphur+Acaricides (WG)

Example 1

Sulphur 60%+Bifenazate 8.5% WG

Step 1: Preparation of 'Additive Mix'

25 parts of Sodium salt of naphthalene sulfonate condensate (eg. Tamol NN 8906), 25 parts of Sodium salt of phenol sulfonate condensate (eg. Tamol PP), 100 parts of Sodium lignin sulfonate (eg. Reax 100M) and 50 parts of Kaolin (eg. Barden clay) are blended together and used as 'additive mix'.

Step 2: Preparation of Mill Base 28.4 parts of 'additive mix' is first dispersed in 100 parts of water. Added slowly 9.6 parts of Bifenazate (95% purity) followed by 62 parts of sulphur technical (99%) to the above dispersion under high shear mixing. The mixture is wet milled using a bead mill to an average particle size of around 2 microns to get the mill base.

Step 3: Spray Granulation of Mill Base

The above mill base is spray granulated in an appropriate spray drier with an out let of a suitable temperature followed by sieving to remove the under sized and oversized, to get Sulphur 60%+Bifenazate 8.5% WG.

Example 2

Sulphur 60%+Bifenazate 17% WG

Mill base prepared by milling a mixture of 20 parts of Bifenazate (95% purity), 62 parts of sulphur technical (99% purity), 18 parts of 'additive mix' in 100 parts of water is spray granulated as in Example 1 to get Sulphur 60%+Bifenazate 17% WG.

Example 3

Sulphur 85%+Bifenazate 1% WG

Mill base prepared by milling a mixture of 1.5 parts of Bifenazate (95% purity), 82 parts of sulphur technical (99% purity), 16.5 parts of 'additive mix' in 100 parts of water is spray granulated as in Example 1 to get Sulphur 85%+Bifenazate 1% WG.

Examples for Sulphur+Acaricides (SC)

Example 4

Sulphur 40.0%+Bifenazate 8.5% SC

Mill base, having an average particle size of around 2 microns, is prepared as in Example 1 by milling a mixture of 9.0 parts of Bifenazate (95% purity), 41.0 parts of sulphur technical (99% purity), 10 parts of 'additive mix' in 27.5 parts of water containing 5 parts of propylene glycol. 7.5 parts of 2% dispersion of xanthum gum (eg. Rhodopol) in water containing 0.5% 1,2-Benzisothiazolin-3-one (eg. Proxel) is then added to the mill base and mixed thoroughly to get Sulphur 40.0%+Bifenazate 7.5% SC.

The efficacy trials conducted using stand-alone treatments of sulphur and acaricide were done in accordance with standard recommended dosages for these active ingredients in India. However, it may be noted that the recommended dosages for each active ingredient may vary as per recommendations in a particular country, soil conditions, the nature of cultivars weather conditions and disease intensity.

Efficacy Trials

Example 1

Bioefficacy of Sulphur Plus Bifenazate

The trial was conducted in 60 m$^2$ large area, subdivided into plots as replication with rows as per treatments. Eight treatments were carried out with as indicated in the table below. Bifenazate 24% SC and Sulphur 80% WG were used individually as a standard for comparison along with an untreated control.

Treatments were applied with knapsack sprayer. The strawberry mite population density was estimated just before the first treatment and the observations were conducted after fixed intervals on the $1^{st}$, $3^{rd}$, 5th, $7^{th}$ and $10^{th}$ day after spraying. The samples of the 10 youngest leaves were taken randomly from each replication considering that the mite usually prefer infesting the youngest leaves. The number of motile forms and eggs were counted separately on leaves, by using stereoscopic microscope. The results were tabulated as follows:

TABLE 1

Represent the mortality percentage as observed after $10^{th}$ day of spray

| Treatment | Compositions | Active ingredient (grams/hectare) | Formulation dosage in gm/ha | Mortality % of eggs | Mortality of mobile phase of mite (Adult and Juvenile stages) |
|---|---|---|---|---|---|
| 1 | Sulphur 60% + Bifenazate 15% WDG | 900 + 225 | 1500 | 32 | 74 |
| 2 | Sulphur 70% + Bifenazate 13% WDG | 1050 + 195 | 1500 | 28 | 82 |
| 3 | Sulphur 80% + Bifenazate 6% WDG | 1200 + 90 | 1500 | 16 | 70 |
| 4 | Sulphur 40% + Bifenazate 7.5% SC | 600 + 112.5 | 1500 | 28 | 72 |
| 5 | Sulphur 30% + Bifenazate 5% SC | 450 + 75 | 1500 | 16 | 48 |
| 6 | Sulphur 80% WG | 1250 | 1500 | 16 | 62 |
| 7 | Bifenazate 24% SC | 144 | 500 | 18 | 65 |
| 8 | Untreated control | — | — | Nill mortality | Nill mortality |

It was observed that the combination of Sulphur and Bifenazate effectively controlled the nymphal/juvenile and adult stages of mite population. It was observed that the treatments with Sulphur 70%+Bifenazate 13% WDG at 1050+195 g.a.i per ha (Treatment 2) and Sulphur 60%+Bifenazate 15% WDG at 900+225 g.a.i per ha (Treatment 1) proved to be highly effective and provided enhanced control over the mobile phase of mite population, even after the $12^{th}$ day of spraying. Thus the composition of Sulphur and Bifenazate helps in managing the next generation of pests in particular when the dry weather favours the mite multiplication as observed in Treatment 1 with highest mortality of eggs.

An increased mortality rate of the eggs were also observed with the treatment of Sulphur 60%+Bifenazate 15% WDG at 900+225 g.a.i per ha (Treatment 1) as compared to the individual treatment of actives (Treatment 6 and 7).

The combination treatments of Sulphur with Bifenazate resulted in an improved crop yield increased flowering and fruiting and improved foliage (darker greenish colouration of the leaves) showing longer life of the suckers for repetitive fruiting.

In the case of SC formulation, the application of Sulphur 40%+Bifenazate 7.5% SC at 600+112.5 g.a.i per ha (Treatment 4) proved highly effective in controlling the mite population as compared to the individual application with Sulphur 80% WG at 1250 g a.i per ha. (Treatment 6)

two spotted spider mite, T. urticae in brinjal ecosystem. The local ruling variety Covai Vari Kathari was raised with a spacing of 60×60 cm in a plot size of 5×4 m fitting in randomized block treatment and replicated thrice with nine treatments including an untreated control as indicated in the table below. The cultural operations were followed uniformly to all the plots.

Pre-treatment count was recorded to assess the uniformity of mite occurrence and mite load enough to cause injury to crop. The post-treatment counts were recorded on $1^{st}$ $3^{rd}$, $7^{th}$ and the $14^{th}$ day after the spraying. The spraying was done fortnightly. The mite population and the egg count were observed from 10 randomly selected plants per plot, selecting three leaves per plant and from each leaf 2 $cm^2$ area was marked for counting mites using a square card and 10× hand lens. The mean population of the mite was worked out from which the percentage mortality was worked for each spray.

The applications were conducted as indicated in the table below:

TABLE 2

| Treatment | Compositions | Active ingredients (grams/hectare) | Formulation Dosage in grams/hectare | Eggs Mortality % after $5^{th}$ DAS | Mortality % after $5^{th}$ DAS on Juvenile & Adults |
|---|---|---|---|---|---|
| 1 | Sulphur 70% + Fenpyroximate 4% WDG | 1050 + 60 | 1500 | 68 | 90 |
| 2 | Sulphur 65% + Fenpyroximate 2% WDG | 975 + 30 | 1500 | 58 | 78 |
| 3 | Sulphur 65% + Fenpyroximate 1.5% WDG | 975 + 22.5 | 1500 | 52 | 70 |
| 4 | Sulphur 80% + Fenpyroximate 1% WDG | 1200 + 15 | 1500 | 55 | 80 |
| 5 | Sulphur 40% + Fenpyroximate 1.5% SC | 600 + 22.5 | 1500 | 50 | 75 |
| 6 | Sulphur 32.5% + Fenpyroximate 0.75% SC | 487.5 + 11.25 | 1500 | 30 | 48 |
| 7 | Fenpyroximate 5% SC | 22.5 | 450 | 30 | 65 |
| 8 | Sulphur 80% WG | 1250 | 1500 | 25 | 70 |
| 9 | Untreated (control) | — | — | nill | Nill |

The combination products proved to be better in controlling the adult and the immature stages of the pest complex (mite) in comparison to Bifenazate and Sulphur used alone and in comparison with the untreated control besides delivering the additional benefit of Sulphur as a supplementary nutrient. Such combination further proved to be economically efficient and effective in management of deadly mites and served as a source of nutrition due to presence of Sulphur.

Example 2

Bioefficacy of Sulphur Plus Fenpyroximate

The field study conducted in the Nasik district of Maharashtra state in India, to evaluate the efficacy of certain combinations of Sulphur+Fenpyroximate by keeping Fenpyroximate as a Standard acaricide. All the nine treatments were applied as foliar applications for the management of The impact of the treatments with Fenpyroximate 5% SC, Sulphur 80% WG alone and treatments with Sulphur plus Fenpyroximate were evaluated on Brinjal crop at the time of sufficient infestation of mite, Tetranychus urticae It was observed that treatments with Sulphur 70%+Fenpyroximate 4% WDG at 1050+60 g.a.i per ha (Treatment 1) and Sulphur 65%+Fenpyroximate 2% WDG at 975+30 g.a.i per ha (Treatment 2) exhibited a higher percentage mortality of the mite population in the eggs as well as the juvenile and the adult stages of the mite population as compared to the individual application of Fenpyroximate 5% SC (Treatment 7) and Sulphur 80% WG (Treatment 8)

A high percentage mortality of the mite population in all the stages was also observed with Sulphur 40%+Fenpyroximate 1.5% SC at 600+22.5 g a.i per ha (Treatment 5) in case of the SC formulation as compared to the individual treatment with Sulphur 80% WG at 1250 g. a.i per ha. (Treatment 8) and Fenpyroximate 5% SC at 22.5 g.a.i per ha (Treatment 7).

The result showed that Sulphur+Fenpyroximate in combination was superior in controlling the egg as well as Juvenile and adult population of mite. The composition showed improved foliage (darker greenish colouration of the leaves) and increased flowering and fruiting were also observed. It is to be noted, the reduced rates of Fenpyroximate when used in combination with reduced rates of Sulphur signifying synergistic role in enhanced bioefficacy at critical stages of mite management (Treatment 4)

Example 3

Bioefficacy of Sulphur Plus Fenazaquin

The trial was conducted in the Nasik district of Maharashtra state in India to control two spotted spider mite (*Tetraychus urticae*) which attacks a wide range of garden plants, including many vegetables, fruits and flowers. The trial was conducted in a 60 m² large area, subdivided into plots as replication with rows as per treatments. Eight treatments were conducted including treatment with Fenazaquin 20% SC and Sulphur 80% WG, used alone as standards for comparison, along with one untreated control. The treatments applied are indicated in the table below:

Treatments were applied with knapsack sprayer. The strawberry mite population density was estimated just before the first treatment and the observations were conducted after fixed intervals of $1^{st}$, 3rd, 5th $7^{th}$ and $10^{th}$ day after spraying. The sample of the 10 youngest leaves was taken randomly from each replication understanding that the mites usually prefer the youngest leaves. The numbers of motile forms were counted separately on leaves, by using stereoscopic microscope. The results were tabulated as follows:

TABLE 3

| Treatment | Compositions | Active ingredient (grams/hectare) | Formulation Dosage in (grams/hectare) | Mortality of motile phase of mite (Adult and Juvenile stages) |
|---|---|---|---|---|
| 1 | Sulphur 55% + Fenazaquin 30% WDG | 825 + 450 | 1500 | 86 |
| 2 | Sulphur 70% + Fenazaquin 15% WDG | 1050 + 225 | 1500 | 80 |
| 3 | Sulphur 75% + Fenazaquin 10% WDG | 1125 + 150 | 1500 | 82 |
| 4 | Sulphur 37.5% + Fenazaquin 8.5% SC | 562.5 + 127.5 | 1500 | 68 |
| 5 | Sulphur 70% + Fenazaquin 5% SC | 1050 + 75 | 1500 | 72 |
| 6 | Sulphur 80% WG | 1250 | 1500 | 63 |
| 7 | Fenazaquin 20% SC | 250 | 1250 | 68 |
| 8 | Untreated control | — | — | Nill mortality |

It was observed that the combination of Sulphur and Fenazaquin effectively controlled the nymph/juvenile and adult stages of mite population and provided good control over the mobile phase of mite population.

It was found that while, Treatments 1, 2 and 3 with 825+450, 1050+225 and 1125+150 g.a.i. per ha were effective in controlling the mite population in motile phases of its life cycle as compared to treatment 7 with Fenazaquin 20% SC alone. Particularly, Sulphur 75%+Fenazaquin 10% WDG at 1125+150 g.a.i per ha (Treatment 3) demonstrated maximum mortality signifying the synergistic effect of the composition with the dosage of Fenazaquin reduced to half as compared to the solo application of Fenazaquin (Treatment 7).

It was further observed that Treatment 5 with Sulphur 70%+Fenazaquin 5% SC at 1050+75 g.a.i per ha, effectively controlled the mite population in comparison with the individual Treatment 6 and Treatment 7 of both the actives.

It can be concluded that the combination product was better in controlling the adult and immature stages of two spotted spider mite in comparison to Fenazaquin used alone. The combination product with Sulphur was found to be better for the mobile stages of pest in comparison to the untreated control.

It was noted that significant mortality of mites was observed at low dosage of fenazaquin when combined with Sulphur, also the addition of Sulphur to the composition showed improved foliage (darker greenish colouration of the leaves) and increased flowering and fruiting was also observed due to the presence of sulphur which served as a nutrient in the tested combinations.

Example 4

Bioefficacy of Sulphur Plus Hexythiazox

The trial was conducted on brinjal (*Solanum melongena*) for both ovicidal and larvicidal effects on two spotted spider mite (*Tetranychus urticae* Koch) in Green house condition under randomized block design by growing Brinjal in pot condition with five replications and nine treatments. In the experiment, treatments were imposed after sufficient build up of *Tetranychus urticae* Koch population on a plot size of 4 m×4 m.

The pre and post treatment observations on live red spider mite populations were assessed on the $2^{nd}$, $5^{th}$, $7^{th}$ and $10^{th}$ day after spraying.

Mite growth regulator (Hexythiazox) was combined with the contact acaricide (Sulphur), to evaluate its ovicidal and acaricidal impact on metamorphosis stages of *T. urticae*.

Three leaves covering the top, middle and the bottom canopy of crops were selected from each treatment and the observations were taken from those leaves in all the replications and the microscopic lens was used to see the different stages of mites. On visual inspection, 60% of the leaves were attacked by mite infestation.

The treatments were conducted as mentioned in the table below:

TABLE 4

| Treatment | Compositions | Active ingredients (grams/hectare) | Formulation Dose grams/hectare | Eggs Mortality % after $5^{th}$ DAS | Mortality % after $5^{th}$ DAS on Juvenile & Adults |
|---|---|---|---|---|---|
| 1 | Sulphur 70% + Hexythiazox 4% WDG | 700 + 40 | 1000 | 88 | 90 |
| 2 | Sulphur 60% + Hexythiazox 2% WDG | 600 + 20 | 1000 | 82 | 85 |
| 3 | Sulphur 80% + Hexythiazox 2% WDG | 800 + 20 | 1000 | 92 | 90 |

TABLE 4-continued

| Treatment | Compositions | Active ingredients (grams/hectare) | Formulation Dose grams/hectare | Eggs Mortality % after 5th DAS | Mortality % after 5th DAS on Juvenile & Adults |
|---|---|---|---|---|---|
| 4 | Sulphur 80% + Hexythiazox 1% WDG | 800 + 10 | 1000 | 80 | 80 |
| 5 | Sulphur 40% + Hexythiazox 1.5% SC | 400 + 15 | 1000 | 75 | 80 |
| 6 | Sulphur 30% + Hexythiazox 0.75 SC | 300 + 7.5 | 1000 | 45 | 65 |
| 7 | Hexythiazox 5.45% EC | 27.25 | 500 | 68 | 60 |
| 8 | Sulphur 80% WG | 1250 | 1500 | 30 | 75 |
| 9 | Untreated (control) | — | — | Nill | Nill |

It was found that the application of Sulphur 80%+ Hexythiazox 2% WDG at 800+20 g.a.i per ha (Treatment 3) showed the highest egg mortality as compared to Hexythiazox 5.45% EC at 27.25 g.a.i per ha (Treatment 7). It is to be noted, that the reduced rates of Hexythiazox when used in combination with Sulphur signifies a synergistic effect of the combination with enhanced bioefficacy at critical stages of mite management.

As an adulticide, the applications of Sulphur 70%+ Hexythiazox 4% WDG at 700+40 g a.i per ha (Treatment 1) and Sulphur 80%+Hexythiazox 2% WDG at 800+20 g a.i per ha (Treatment 3) were also found significantly superior as compared to the individual application of Hexythiazox 5.45% EC at 27.25 g.a.i per ha (Treatment 7).

A relatively higher percentage of mortality of the mite population in all the stages was observed with Sulphur 40%+Hexythiazox 1.5% SC at 400+15 g a.i per ha (Treatment 5) in case of SC formulation as compared to the individual application of Sulphur 80% WG at 1250 g.a.i per ha (Treatment 8) at a higher concentration signifying the synergistic role of SC formulation. This shows the utility of such compositions as compared to stand alone application.

Example 5

Bioefficacy of Sulphur Plus Spirodiclofen

The trial was conducted in 60 m² large area, subdivided into plots as replication with rows to evaluate the control of the strawberry mite, *Phytonemus pallidus* spp. which is the key pest of strawberry in Igatpuri area of Nasik district in Maharashtra state in India. Eight treatments including treatment with Spirodiclofen 24% SC alone was used as a standard for comparison along with an untreated control.

Treatments were applied with knapsack motor sprayers. The strawberry mite population density was estimated just before the first treatment and the observations were conducted at fixed intervals of 1st 3rd, 5th, 7th and 10th day after spraying. The sample of the 10 youngest leaves was taken randomly from each replication considering that the mites usually prefer the youngest leaves for infestation. The number of motile forms and eggs were counted separately on these leaves, by using stereoscopic microscope.

TABLE 5

| Treatment | Compositions | Active ingredient (grams/hectare) | Formulation dosage in gm/ha | Mortality % of eggs | Mortality % of motile phase of mite (Adult and Juvenile stages) |
|---|---|---|---|---|---|
| 1 | Sulphur 60% + Spirodiclofen 15% WDG | 900 + 225 | 1500 | 72 | 90 |
| 2 | Sulphur 70% + Spirodiclofen 9% WDG | 1050 + 135 | 1500 | 68 | 85 |
| 3 | Sulphur 80% + Spirodiclofen 5% WDG | 1200 + 75 | 1500 | 55 | 77 |
| 4 | Sulphur 40% + Spirodiclofen 5% SC | 600 + 75 | 1500 | 68 | 80 |
| 5 | Sulphur 30% + Spirodiclofen 2.5% SC | 450 + 37.5 | 1500 | 34 | 55 |
| 6 | Sulphur 80% WG | 1250 | 1500 | 22 | 68 |
| 7 | Spirodiclofen 24% SC | 144 | 500 | 34 | 70 |
| 8 | Untreated control | — | — | — | — |

It was observed that the combination of Sulphur and Spirodiclofen effectively controlled the nymphal/juvenile and adult stages of mite population and provides very effective control over the eggs population thereby displayed a good ovicidal action as well.

It was observed that the treatments with Sulphur 60%+ Spirodiclofen 15% WDG at 900+225 g.a.i per ha (Treatment 1) and Sulphur 70%+Spirodiclofen 9% WDG at 1050+135 g.a.i per ha (Treatment 2) proved to be effective in controlling the adult and immature stages of pest complex (mite) with reduced dosages of the actives as compared to Spirodiclofen 24% SC at 144 g.a.i per ha (Treatment 7) used alone.

It was also observed that treatment with Sulphur 40%+ Spirodiclofen 5% SC at 600+75 g a.i per ha (Treatment 4) was effective in controlling the mite population as compared to the individual treatments at higher concentrations (Treatments 6 and 7).

It was noted that Treatment 1 and 2 showed longer residual control even up to 15 DAS than all other treatments further signifying the synergistic impact.

Example 6

Bioefficacy of Sulphur Plus Spiromesifen

The trial was conducted in 5 m×4 m area plot with nine treatments including a treatment with Spiromesifen 22.9% SC, alone as a standard for comparison along with one untreated control to control Red spider mite which is an occasional pest of cotton in all the cotton growing areas.

The overall infestation and attack of mite and white fly was sufficient as the average count of adult white fly on 55 day old cotton crop was 90 adult white flies (top+middle+ bottom leaf) and the nymph stages averaged 132 (all together three leaf) whereas, adult mites averaged 68 (top+ middle+bottom leaf) and Juvenile stages were 92 (Top+ Middle+bottom leaf).

The treatments were as indicated in the table below:

TABLE 6

| Treatment | Compositions | Active ingredient (gram/hectare) | Formulation Dosage in g/ha | Mortality % of egg (White fly) | Mortality % of egg (mite) | WHITE FLY (%) control- 5$^{th}$ day after spray | | MITE (%) control- 5$^{th}$ day after spray | |
|---|---|---|---|---|---|---|---|---|---|
| | | | | | | ADULT | NYMPH | ADULT | JUVENILE |
| 1 | Sulphur 60% + Spiromesifen 10% WDG | 900 + 150 | 1500 | 40 | 33 | 48 | 72 | 64 | 80 |
| 2 | Sulphur 70% + Spiromesifen 7% WDG | 1050 + 105 | 1500 | 38 | 38 | 62 | 78 | 77 | 87 |
| 3 | Sulphur 50% + Spiromesifen 6% WDG | 750 + 90 | 1500 | 29 | 28 | 50 | 75 | 65 | 72 |
| 4 | Sulphur 60% + Spiromesifen 4% WDG | 900 + 60 | 1500 | 32 | 32 | 38 | 70 | 60 | 66 |
| 5 | Sulphur 35% + Spiromesifen 3.5% SC | 525 + 52.5 | 1500 | 38 | 35 | 55 | 70 | 70 | 75 |
| 6 | Sulphur 25% + Spiromesifen 2.5% SC | 375 + 37.5 | 1500 | 15 | 12 | 18 | 20 | 30 | 44 |
| 7 | Spiromesifen 22.9% SC | 96 | 500 | 38 | 30 | 42 | 60 | 42 | 64 |
| 8 | Sulphur 80% WG | 1250 | 1500 | 7 | 10 | 11 | 9 | 38 | 40 |
| 9 | Untreated control | — | — | | | | | | |

It was observed that applications of Sulphur 60%+Spiromesifen 10% WDG at 900+150 g a.i. per ha (Treatment 1) and Sulphur 70%+Spiromesifen 7% WDG at 1050+105 g a.i. per ha (Treatment 2) proved to be effective in controlling the adult and immature stages of pest complex (white fly and mite) in comparison to Spiromesifen22.9% SC at 96 g.a.i per ha (Treatment 7) used alone.

It was also found that application of Sulphur 35%+Spiromesifen 3.5% SC at 525+52.5 g a.i.per ha (Treatment 5) was found highly effective in controlling the mite population as compared to the application of Sulphur 80% WG applied alone at a higher concentration (Treatment 8). This demonstrates the synergistic effect of composition comprising Sulphur and spiromesifen at much reduced rates.

It was observed that the combination of Sulphur and Spiromesifen effectively controlled the nymphal and juvenile stages of white fly and mite population. The combination also exhibits a good ovicidal activity.

The combination of sulphur with Spiromesifen proved to control all the stages of mites effectively. It was also observed that Sulphur added to the compositions (Treatments 1-6) also exhibited enhanced flowering and fruiting and an improved foliage (darker greenish coloured leaves) and better resistance to lodging because of un expected high wind storms (observed in this treatment areas). It is possible that the resistance to abiotic factors can be related to the role of Sulphur.

These combinations can be useful in field situations where both the pests occur at the same time on several crops and under uncertain conditions of nature. The combination can also be used in managing broad spectrum of the pest, thus proving economical benefit to the user.

Example 7

Bioefficacy of Sulphur Plus Bifenthrin

The okra crop cultivar Mayhcho 10 was raised in randomized block design with five treatments replicated thrice in 20 m$^2$ plot size. The treatments used are as indicated in the Table 7 below:

The spraying was done at the beginning of the flowering/fruiting stage. A control with only water spray was maintained for comparison.

The population of immature active stages and adults in all the treatments were counted a day prior to the first spray treatment.

TABLE 7

| Treatment | Compositions | Active ingredient (grams/hectare) | Formulation dosage in g/ha | Mortality on % after 5$^{th}$ DAFS |
|---|---|---|---|---|
| 1 | Sulphur 60% + Bifenthrin 7% WDG | 900 + 105 | 1500 | 88 |
| 2 | Sulphur 70% + Bifenthrin 4% WDG | 1050 + 60 | 1500 | 75 |
| 3 | Sulphur 80% + Bifenthrin 2% WDG | 1200 + 30 | 1500 | 55 |
| 4 | Sulphur 40% + Bifenthrin 2.5% SC | 600 + 37.5 | 1500 | 70 |
| 5 | Sulphur 30% + Bifenthrin 1.5% SC | 450 + 22.5 | 1500 | 46 |
| 6 | Bifenthrin 10% EC | 60 | 600 | 58 |
| 7 | Sulphur 80% WG | 1250 | 1500 | 64 |
| 8 | Untreated control | — | — | 0 |

At 5 days after first spray (DAFS), the application of Sulphur 60%+Bifenthrin 7% WDG at 900+105 g.a.i per ha (Treatment 1) and Sulphur 70%+Bifenthrin 4% WDG at 1050+60 g.a.i per ha (Treatment 2) particularly proved to be highly effective in controllling the mite population as compared to the application of Bifenthrin alone at a similar concentration. (Treatment 6).

The incidence of mite reoccurrence in the other treatments (Treatment 1 and 2) were observed after the 20$^{th}$ day of the first spray. The composition played an important role in delaying the reoccurrence of pest population.

It was also visually noticed that treatments in combination with Sulphur were observed to have minimum powdery mildew infection as compared to the stand alone application (Treatment 6 and 7). And the combination of Sulphur+Bifenthrin treatments observed lesser populations of sucking pests, chewing pests and showing broad spectrum of management which is needed today to maintain an ecofriendly environment.

It was also observed that effective control of the mite population was achieved with Sulphur 40%+Bifenthrin 2.5% SC at 600+37.5 g.a.i per ha (Treatment 4) as compared to the individual treatment of the actives.

Moreover, the phytotonic effect in the form of increased greenery of the leaves was observed in all the treatments (Treatments 1-5) where Sulphur was used in combination with Bifenthrin. It was observed that the presence of Sulphur in the composition also resulted in an enhanced flowering, fruiting and also more number of pickings at early stage giving higher returns to the end use. The combination not only managed powdery mildew but also controlled population of sucking pests and Chewing pests.

Example 8

Bioefficacy of Sulphur and Abamectin

The trial were conducted in Akola district of Maharashtra state in India on Okra with the treatments as indicated in the table below including compositions of sulphur plus abamectin at varying concentrations, Sulphur 80% WG standalone and Abamectin 1.9% EC standalone as standards for comparison, along with an untreated control. The treatments were laid out on a randomized block design with thirteen treatments replicated five times.

The treatments were imposed after sufficient build up of red spider mites. The pre and post treatment observations on live red spider mite populations were assessed on 2, 5, 7 and 10 days after spray and were repeated twice at an interval of 10 days.

The treatments were as illustrated in the table below:

TABLE 8

| Treatments | Composition | Active ingredients (grams/hectare) | Formulation Dosage in grams/hectare | Mortality (%) of red spider mite, T. macfarlanei after 5$^{th}$ DAS | Live Mite population at 12$^{th}$ days after spray (in percentage) |
|---|---|---|---|---|---|
| 1 | Sulphur 70% + Abamectin 3% WDG | 1050 + 45 | 1500 | 92 | Nill |
| 2 | Sulphur 65% + Abamectin 2% WDG | 975 + 30 | 1500 | 85 | Nill |
| 3 | Sulphur 65% + Abamectin 1.5% WDG | 975 + 22.5 | 1500 | 76 | 4 |
| 4 | Sulphur 80% + Abamectin 1.5% WDG | 1200 + 22.5 | 1500 | 75 | 2 |
| 5 | Sulphur 85% + Abamectin 1% WDG | 1275 + 15 | 1500 | 66 | 7 |
| 6 | Sulphur 90% + Abamectin 0.5% WDG | 1350 + 7.5 | 1500 | 58 | 13 |
| 7 | Sulphur 90% + Abamectin 0.2% WDG | 1350 + 3.0 | 1500 | 50 | 16 |
| 8 | Sulphur 90% + Abamectin 0.08% WDG | 1350 + 1.2 | 1500 | 48 | 23 |

TABLE 8-continued

| Treatments | Composition | Active ingredients (grams/hectare) | Formulation Dosage in grams/hectare | Mortality (%) of red spider mite, T. macfarlanei after 5$^{th}$ DAS | Live Mite population at 12$^{th}$ days after spray (in percentage) |
|---|---|---|---|---|---|
| 9 | Sulphur 40% + Abamectin 1.5% SC | 600 + 22.5 | 1500 | 88 | Nill |
| 10 | Sulphur 32.5% + Abamectin 0.75% SC | 487.5 + 11.25 | 1500 | 68 | 9 |
| 11 | Abamectin 1.9% EC | 10 | 533 | 63 | 7 |
| 12 | Sulphur 80% WG | 1250 | 1500 | 70 | 8 |
| 13 | Untreated control | — | — | Nill | 38 |

The table indicates that application, of Sulphur 70%+Abamectin 3% WDG at 1050+45 g a.i per hectare (Treatment 1) and Sulphur 65%+Abamectin 2% WDG at 975+30 g a.i per hectare (Treatment 2) were found to be highly effective in controlling red spider mites on leaf area in comparison to the standard Abamectin 1.9% EC at 10 g a.i per hectare (Treatment 11) used alone.

The other two compositions of Sulphur 65%+Abamectin 1.5% WDG at 975+22.5 g a.i per hectare and Sulphur 80%+Abamectin 1.5% WDG 1200+22.5 g a.i. per hectare (Treatment 3, 4), were also found superior in controlling red spider mites than Abamectin 1.9% EC at 10 g a.i per hectare (Treatment 11) used alone and Sulphur 80% WG at 1250 g a.i. per ha (Treatment 12) used alone. It was also observed that residual impact of combination avoided resurgence in mite population after 12$^{th}$ days of application.

In case of SC formulations, the application of Sulphur 40%+Abamectin 1.5% SC at 600+22.5 g a.i. per ha (Treatment 9) proved highly effective in reducing the mite population as compared to the individual application with sulphur 80% WG at 1250 g a.i. per ha (Treatment 12).

It was also observed that with application, of Sulphur 70%+Abamectin 3% WDG at 1050+45 g a.i per ha (Treatment 1) and Sulphur 65%+Abamectin 2% WDG at 975+30 g a.i per ha (Treatment 2) and Sulphur 80%+Abamectin 1.5% WDG at 1200+22.5 g a.i per hectare (Treatment 3) highest fruit yield of 250 quintal, 245 quintal and 230 quintal each per ha was recorded in comparison with the yield of Abamectin 1.9% EC at 10 g a.i per hectare (Treatment 11) and Sulphur 80% WG at 1250 g a.i. per hectare (Treatment 12), wherein the yield was found to be 220 quintal & 210 quintals respectively. Thus composition of sulphur and abamectin gave an increased yield of 10 quintals on an average as compared to the stand alone application of the active ingredients The combination treatments of Sulphur with Abamectin resulted in an increased flowering and fruiting and improved foliage (darker greenish colouration of the leaves). It also enhanced the early and good quality first fruit picking thereby showing healthy stand of crop intern managing overlapping generations of mites below Economic Threshold Level (ETL).

From the foregoing it will be observed that numerous modifications and variations can be effectuated without departing from the true spirit and scope of the novel concepts of the present invention. It is to be understood that no limitation with respect to the specific embodiments illustrated is intended or should be inferred.

I claim:

1. A synergistic pesticidal composition comprising sulphur in the range of 30% to 80% w/w of the total composition and at least one acaricide selected from the group consisting of bifenazate in the range from 5% to 15% w/w of the total composition, fenpyroximate in the range from 0.75% to 4% w/w of the total composition, fenazaquin in the range from 5% to 30% w/w of the total composition, hexythiazox in the range of 0.75% to 4% w/w of the total composition, spirodiclofen in the range of 2.5% to 15% w/w of the total composition, spiromesifen in the range from 2.5% to 12% w/w of the total composition, or their salts and at least one agrochemically acceptable excipient; wherein said synergistic pesticidal composition exhibits superior pesticidal efficacy compared with a pesticidal composition comprised of either sulphur or acaricide alone.

2. The synergistic pesticidal composition of claim 1, wherein the composition is in a solid form or a liquid form.

3. The synergistic pesticidal composition of claim 1, wherein the composition is in the form of gels, suspo emulsions, capsulated suspension, emulsion in water, oil dispersion, water dispersible granules, suspension concentrates, wettable powders, emulsifiable concentrates and seed dressing.

4. The synergistic pesticidal composition of claim 1, wherein the composition is in the form of water dispersible granules comprising sulphur in the range of 50% to 80% w/w of the total composition and at least one acaricide in the range of 1% to 30% w/w of the total composition.

5. The synergistic pesticidal composition of claim 1, wherein the composition is in the form of suspension concentrate comprising sulphur in the range of 25% to 80% w/w of the total composition and at least one acaricide in the range of 0.75 to 10% w/w of the total composition.

6. A pesticidal composition consisting of sulphur in the range of 30% to 80% w/w of the total composition and bifenthrin or its salt in the range of 1.5% to 7% w/w of the total weight of the composition and at least one agrochemically acceptable excipient.

7. A pesticidal composition consisting of sulphur in the range of 32.5% to 90% w/w of the total composition, abamectin or salt thereof in the range of 0.08% to 3.6% w/w of the total composition and at least one agrochemically acceptable excipient.

* * * * *